US006962690B2

(12) United States Patent
Kiefer et al.

(10) Patent No.: US 6,962,690 B2
(45) Date of Patent: Nov. 8, 2005

(54) TISSUE SPECIFIC FLUORESCENT CHELATES POSSESSING LONG WAVELENGTH UV EXCITATION

(75) Inventors: Garry E. Kiefer, Lake Jackson, TX (US); Darryl J. Bornhop, Lubbock, TX (US)

(73) Assignees: Dow Global Technologies Inc., Midland, MI (US); Texas Tech University, Lubbock, TX (US)

( * ) Notice: Subject to any disclaimer, the term of this patent is extended or adjusted under 35 U.S.C. 154(b) by 52 days.

(21) Appl. No.: 10/278,584

(22) Filed: Oct. 22, 2002

(65) Prior Publication Data

US 2003/0099598 A1 May 29, 2003

Related U.S. Application Data

(60) Provisional application No. 60/355,684, filed on Oct. 22, 2001.

(51) Int. Cl.$^7$ ............................ A61B 10/00; A61B 5/00; A61B 8/00
(52) U.S. Cl. ...................... 424/9.6; 424/1.11; 424/1.65; 424/9.1; 424/9.3; 424/9.362; 424/9.7; 424/9.8; 534/14; 540/450; 540/460; 540/474
(58) Field of Search .............................. 424/7.11, 1.65, 424/9.1, 9.2, 9.3, 9.4, 9.5, 9.6, 9.7, 9.8, 9.362; 534/7, 10–16; 540/450, 460, 474

(56) References Cited

U.S. PATENT DOCUMENTS

| 4,920,195 A | 4/1990 | Kankare et al. ............... 534/16 |
| 4,976,950 A | 12/1990 | Simon et al. ................. 424/1.1 |
| 5,312,922 A | 5/1994 | Diamandis ................... 546/156 |
| 5,928,627 A | 7/1999 | Kiefer et al. ............... 424/968 |
| 2003/0129579 A1 * | 7/2003 | Bornhop et al. ................ 435/4 |

FOREIGN PATENT DOCUMENTS

| WO | WO 94/26275 | 11/1994 |
| WO | WO 94/26753 | 11/1994 |
| WO | WO 97/40055 | 10/1997 |

OTHER PUBLICATIONS

Griffin, J. M. M., et al, "Simple, high yielding synthesis of trifunctional fluorescent lanthanide chelates", *Tetrahedron Letters* 42 (2001) 3823–3825.

Baden, E. "Prevention of Cancer of the Oral Cavity and Pharynx," *CA Cancer Journal for Clinicians*, vol. 31, No. 1, 1987, pp. 49–62.

Cacheris, W. P. et al., "Thermodynamic study of Lanthanide Complexes of 1,4,7–Triazacyclononane–N,N'N"–triacetic Acid and 1,4,7,10–Tetraazacyclododecane–N.,N',N", N'"–tetraacetic Acid," *Inorganic Chem*, vol. 26, 1987, pp. 958–960.

Devoisselle, J. M. et al., "Measurement of in vivo fumorous/normal tissue pH by localized spectroscpy using a fluorescent marker," *Optical Engineering*, vol. 32, No. 2 193, pp. 239–243.

Diamandis, E. P and Christopoulos, T. K., "Europium Chelate labels in Time–Resolved Fluorescence Immunoassays and DNA Hybridization Assays," *Analytical Chemistry*, vol. 62, No. 22, 1990, pp. 1149A–1157A.

Diamandis, E. P., "Immunoassays with Time–Resolved Fluorescence Spectrscopy: Principles and Applications," *Clinical Biochemistry* vol. 21, Jun. 1988, pp. 139–150.

Diamandis, E. P., Analytical Methodology for Immunoassays and DNA Hybridization Assays–Current Status and Selected Systems–Critical Review *Clinica Chimica Acta.*, vol. 194, 1990, pp. 19–50.

Griffin, J. M. M. et al., "Simple, High Yielding Synthesis of Trifunctional Fluorescent Lanthanide Chelates," *Tetrahedron Letters*, vol. 42, 2001, pp. 1–3.

Gross, D. J., "Quantitative Single Cell Fluorescence Imaging of Indicator Dyes," *Noninvasive Techniques in Cell Biology*, Wiley–Liss Publishers, New York, NY, 1990, Chap. 2, pp. 21–51.

Haugland, R. P. and Minta, A., "Design and Application of Indicator Dyes," *Noninvasive Techniques in Cell Biology*, Wiley–Liss Publishers, New York, NY, 1990, Chap. 1, pp. 1–20.

Kallistratos, G., "Fluorescent Properties of Aromatic Complexes with Rare Earths and Other Elements of the IIIa Group," *Chemika Chronika, New Series*, vol. 11, 1982, pp. 249–266.

Kim, W. D., et al., "Relaxometry, Luminescence Measurements, Electrophoresis, and Animal Biodistribution of Lanthanide (III) Complexes of Some Polyaza Macrocyclic Acetates Containing Pyridine," *Inorganic Chem.*, vol. 34, 1995, p. 2233–2243.

Latva, M. et al., "Correlation Between the Lowest Triplet State Energy Level of the Ligand and Lanthanid (III) Luminescence Quantum Yield," *Journal of Luminescence*, vol. 75, 1994, pp. 149–169.

(Continued)

*Primary Examiner*—Dameron L. Jones
(74) *Attorney, Agent, or Firm*—Elisabeth T. Jozwiak

(57) ABSTRACT

Fluorescent chelates of lanthanide, terbium, europium and dysprosium with tetraazamacrocyclic compounds are discussed which can be used as fluorescent in vitro or in vivo diagnostic agents. These chelates are tissue specific imaging agents for soft tissue cancers.

19 Claims, 2 Drawing Sheets

OTHER PUBLICATIONS

Marks, P. H. and Schechter, F. G., "Multiple Primary Carcinomas of the Hand, Neck, and Lung," *The Annals of Thorac Surgery* vol. 33, No. 4, Apr. 1982, pp. 324–332.

Silverman Jr., S. and Gorsky, M., "Epidemiologic and Demographic Update in Oral Cancer: California and National Data 1973–1985," *Journal of Am. Dent. Assoc.* vol. 120 No. 5, May 1990 pp. 495–499.

Soini, E. and Lovgren, T., "Time–Resolved Fluoescence of Lanthanide Probes and Applications in Biotechnology," *Crit. Rev. Anal. Chem.* vol. 18, 1987, pp. 105–154.

Varbec, D. P., "Multiple Primary Malignancies Associated with Index Cancers of the Oral, Pharyngeal and Laryngeal Areas," *Trans. Pa. Acad. Opthalmol. Otolaryngol.*, vol. 32 No. 2, 1979, pp. 177–181.

* cited by examiner

TISSUE SPECIFIC FLUORESCENT CHELATES POSSESSING LONG WAVELENGTH UV EXCITATION

This application claims the benefit of provisional application No. 60/355,684 filed Oct. 22, 2001.

FIELD OF THE INVENTION

This invention concerns visual, tissue specific lanthanide, terbium, europium or dysprosium chelates that can be used as visual contrast enhancement agents or diagnostic agents.

BACKGROUND OF THE INVENTION

Fluorescence imaging is found at the heart of numerous chemical and biomedical analysis schemes. Many of these schemes are based on the introduction of a fluorescent species as a marker, stain, dye or indicator [J-M. Devoisselle et al., Optical Engineering 32(2), 239 (1993); R. P. Haugland and A. Minta, "Design and Application of Indicator Dyes," Noninvasive Techniques in Cell Biol., ed. B. H. Satir, Chap. 1, p 1, (Wiley-Liss, New York, N.Y., 1990); D. J. Gross, "Quantitative Single Cell Fluorescence Imaging of Indicator Dyes," Noninvasive Techniques in Cell Biol., ed. B. H. Satir, Chap. 2, p 21, (Wiley-Liss, New York, N.Y., 1990)].

Organic chelates derived from lanthanide ions have become increasingly important as sensitive fluorescent markers for time resolved fluorometric assays [E. P. Diamandis, Clin. Biochem. 21, 139–150 (1988); Clin. Chim. Acta. 194, 19–50 (1990); Anal. Chem. 62, 11 49A–11 57A (1990); E. Soini and T. Lovgren, Crit. Rev. Anal. Chem. 18, 105–154 (1987)]. In particular, terbium and europium complexes are of significant value for these applications because of the efficient fluorescent emission in the visible region (E. P. Diamandis, U.S. Pat. No. 5,312,922). Both of these ions display a weak fluorescent emission in their non-complexed form, but when chelated with an appropriate organic ligand this visible emission is dramatically enhanced. Thus, the organic ligand acts as an antenna for absorbing ultraviolet radiation and transferring this energy to the metal ion that then dissipates the absorbed energy in the form of visible light. The mechanistic details of this phenomenon are well studied and have been extensively documented [A. P. B. Sinha, Fluorescence and Laser Action in Rare Earth Chelates/Spectroscopy in Inorganic Chemistry Volume II, Academic Press, (1971)].

There are numerous chelates capable of long-lived fluorescence but not all of these complexes are suitable for biological applications, one reason being due to their instability in aqueous media [G. Kallistratos, Fluorescent Properties of Aromatic Complexes with Rare Earths and Other Elements of the IIIa-Group/Chemika Chronika. New Series, 11, 249–266 (1982)]. In fact, a large majority of fluorescent chelates are operative in non-aqueous conditions only. This is largely due to the instability of the complex in aqueous solutions resulting in non-complexed metal being present and quenching of the fluorescent pathway responsible for visible light emission. Ultimately, complexes of this type would not be sensitive markers at low concentrations and would present toxicity problems in vivo because of metal deposition in soft tissue.

In recent years chelating agents based upon tetraazamacrocyclic backbones have proven to be extremely valuable for generating aqueous stable lanthanide chelates. In particular, aminocarboxylate and aminophosphonate chelating agents derived from 1,4,7,10-tetraazacyclododecane have been shown to form highly stable lanthanide chelates [W. P. Cacheris, A. D. Sherry, Inorg. Chem. 26, 958–960 (1987); J. Simón, J. R. Garlich, D. A. Wilson, and K. McMillan, U.S. Pat. No. 4,976,950]. The superior nature of this class of chelates has made them useful for diagnostic and therapeutic medical applications such as magnetic resonance imaging and bone marrow ablation. In addition, certain types of these macrocyclic chelating agents incorporating an aromatic moiety, such as the pyridine nucleus, have displayed very efficient fluorescent properties with terbium and europium (J. Kankare, J. Takalo, and P. Pasanen, U.S. Pat. No. 4,920,195). In this patent Kankare et al. demonstrate that a 14-menber macrocyclic europium chelate containing a pyridine nucleus can be conjugated to human IgG. The resulting conjugate thus contains a highly sensitive fluorescent tag (the chelate) which can be quantified by fluorescent immunoassay procedures.

Use of paramagnetic macrocyclic chelates based upon gadolinium (Gd) as contrast agents for magnetic resonance imaging has attracted considerable attention. The appeal of the lanthanide chelates is directly attributed to their kinetic and thermodynamic stability under the challenging aqueous environment encountered in the human body. Appropriate modifications can be made to this type of ligand that will cause pronounced fluorescence when lanthanides, such as terbium (Tb) and europium (Eu), are at the central core. Kim et al., Inorg. Chem. 34, 2233–43 (1995), have reported a recent study on some potential MRI contrast agents based upon macrocyclic pyridine containing ligands. In this study, the inner sphere water coordination was determined by measuring the fluorescent properties of the terbium and europium chelates.

The importance of macrocyclic lanthanide chelates for medical applications has continued to grow with the development of tissue specific agents. Thus far, applications have focused on chelation of radioactive and paramagnetic metal ions for therapy and diagnosis (J. Simón, J. R. Garlich, D. A. Wilson, K. McMillan, U.S. Pat. No. 4,976,950; examples of gadolinium chelates for MRI are Prohance™ by Squibb and Dotarem™ by Guerbet). However, these chelates do not have any fluorescent properties.

The use of fluorescent chelates as visual tissue specific agents was discussed in U.S. Pat. No. 5,928,627 (G. E. Kiefer and D. J. Bornhop). These are macrocyclic lanthanide chelates that fluoresce when excited with UV light in the relatively short 260–280 nm wavelength range that can be used to detect colon cancer visually when illuminated with UV light.

Each year about 31,000 Americans develop oral cancer (4% of all cancers in males and 2% in females). [E. Baden, CA Cancer J. Clin. 37(1), 49–62(1987).] About half of those cancer persons are dead within 5 years from diagnosis, and of the survivors, many will have disfiguration and/or functional compromise. Thus early diagnosis is important as this could increase survival from 50% to 80% [S. Silverman, Jr. and M. Gorsky, J. Am. Dent. Assoc. 120(5), 495–499 (1990).] The incidence of second primary carconomas in the esophagus and upper aerodigestive tract has been estimated to be between 2–30% [D. P. Varbec, Trans. Pa. Acad. Ophthalmol. Otolaryngol. 32(2), 177–191 (1979); P. H. Marks and F. G. Schechter, Ann. Thorac. Surg. 33(4), 324–332 (1982); J. Gluckman, Laryngoscope 3, 90 (1983)]. Detection of these second primary tumors in the early stages would be advantageous.

The most widely used non-invasive method now used for early detection of oral cancer is gross visualization under white-light illumination. This method can be problematic due to the low visual contrast for abnormal tissue, particularly for early detection of dysplastic and pre-malignant lesions where discrimination of such lesions from non-malignant lesions is very difficult. Spectroscopic techniques have been developed to try to improve early detection. Contrast agents are used to enhance the spectroscopic contrast between normal and diseased tissue. Most contrast agents require systemic administration to be effective, which causes exposure to phototoxicity for the tissues. A non-invasive administration of these contrast agents would be preferred.

Thus far, commercial applications of fluorescent chelates have been restricted primarily to the labeling of proteins and antibodies for immunoassays [E. P. Diamandis, Clinica Chimica Acta 194, 19–50 (1990); U.S. Pat. No. 5,312,922]. Products such as FIAgen™ (CyberFluor Inc., Toronto, Ontario, Canada) are available and utilize the europium chelate of 4,7-bis(chlorosulfonyl)-1,10-phenanthroline-2,9-dicarboxylic acid as the fluorescent label. Fluorescent labels of this type are extremely sensitive and can be detected in the subpicomolar range using time resolved fluorometry.

One of the most important features of diagnostic agents is that they must enhance the accuracy of assessing a disease state. Most frequently this involves delivering the diagnostic agent to a specific organ or soft tissue where a suspected abnormality may be present. Currently, the covalent attachment of a small molecule (i.e., diagnostic fragment) to a large protein or antibody (referred to as "bifunctional") is receiving much attention as the method of choice for achieving tissue specificity.

One such example of a bifunctional molecule is disclosed in Griffin, J. M. M. et al, "Simple, high yielding synthesis of trifunctional fluorescent lanthanide chelates", Tetrahedron Letters 42 (2001) pp. 1–3. Griffin discloses a lanthanide chelating ligand based on the cyclen (1,4,7,10-tetraazacyclododecane) nucleus which possesses a single carboxyl group for conjugation to a biologically active species such as an antibody. However, this method is inherently complex and expensive since it requires the use of a specialized antibody in order to achieve tissue specificity.

Therefore, it would be advantageous to use a small molecule diagnostic agent that would localize in a specific tissue of the body without the need for attachment to a delivery molecule such as an antibody. Furthermore, if a stable, fluorescent lanthanide chelate were to exhibit tissue specificity, it would be possible to visually determine the presence of the chelate by illuminating with the appropriate light source that minimized soft tissue damage. Potential applications would be fluorescent guided surgical procedures, in vivo imaging of bone or soft tissue cell growth or morphology, and examinations of the gastrointestinal tract.

SUMMARY OF THE INVENTION

Figure 1:
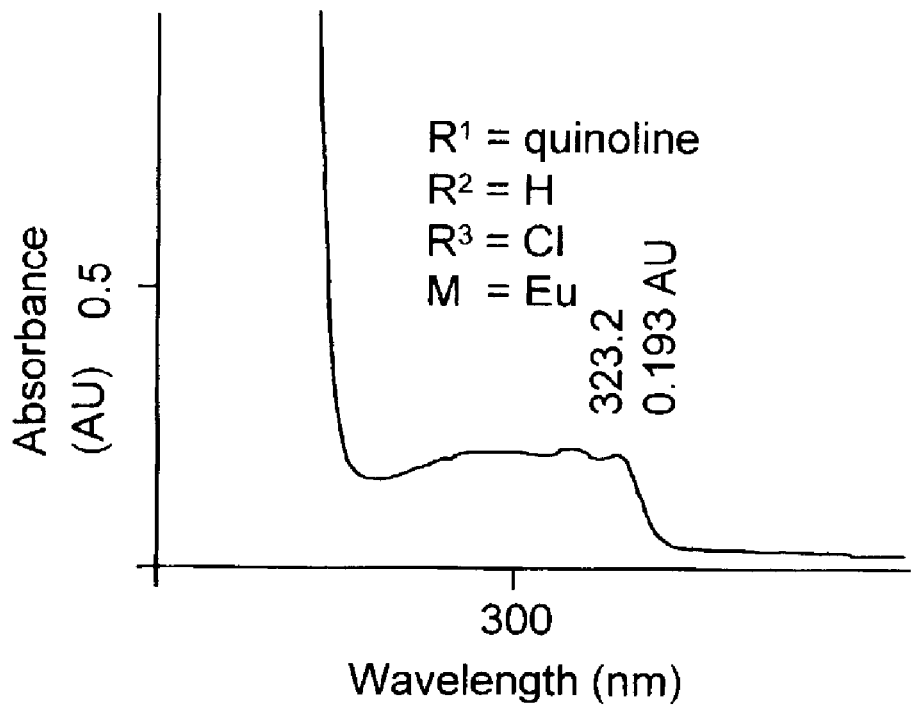
FIG. 1 is the absorption spectra for the europium chelate of Formula (II) where $R^1$ is quinolyl, $R^2$ is H, and $R^3$ is Cl.

The present invention is directed toward novel tissue specific lanthanide, terbium, europium or dysprosium chelates that can be used as visual diagnostic agents. In particular, the preferred chelates are constructed from polyazamacrocyclic compounds of Formula (I) which contain a tetraazacyclododecane trimethylene phosphonic acid nucleus and a pendant ligating moiety which acts as an antenna.

The present invention is directed to novel compounds that are tetraazamacrocyclic compounds of the formula

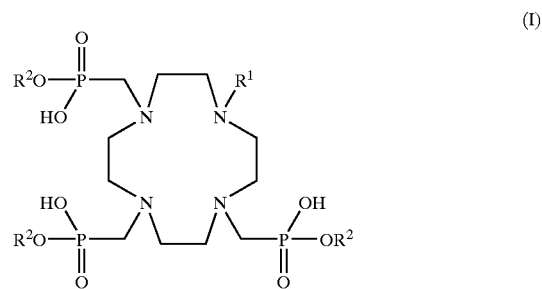

(I)

where: $R^1$ is

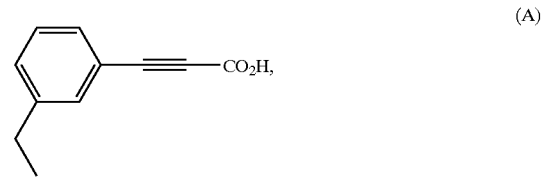

(A)

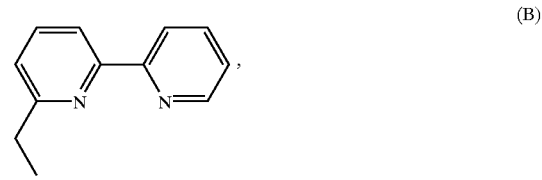

(B)

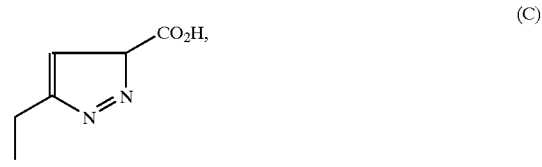

(C)

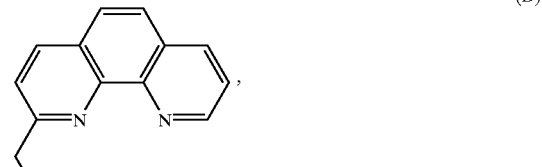

(D)

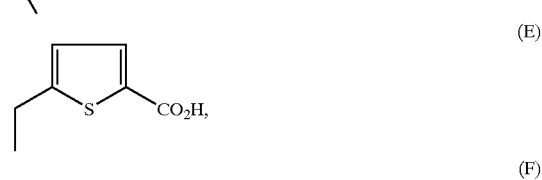

(E)

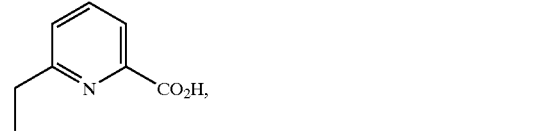

(F)

(G) 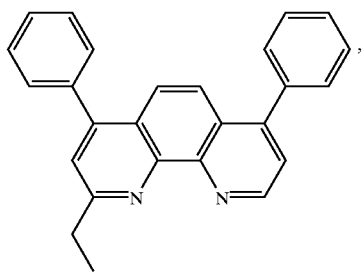
(H) 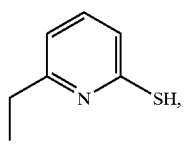
(J) 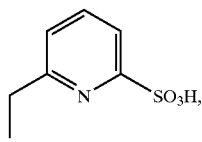
(K) 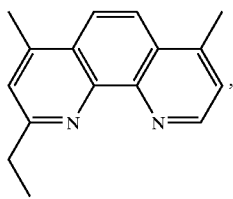
(L) 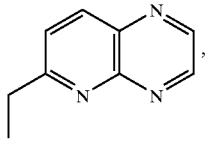
(M) 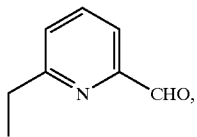
(N) 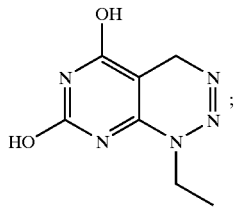
(P) 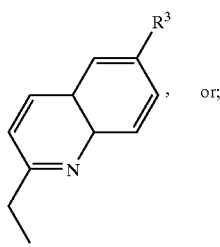, or;
$R^2$ is methyl, ethyl, propyl, butyl or H; and
$R^3$ is F, $C_1$–$C_4$ alkyl, O($C_1$–$C_4$ alkyl) or Cl; or
pharmaceutically acceptable salts thereof.
In another aspect, the present invention is directed to tetraazamacrocyclic chelate compounds of the formula
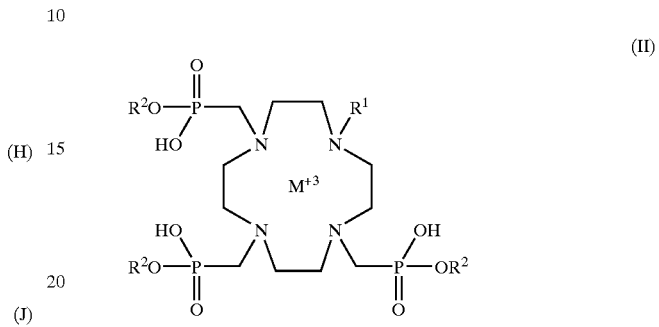 (II)
where: $R^1$ is
(A) 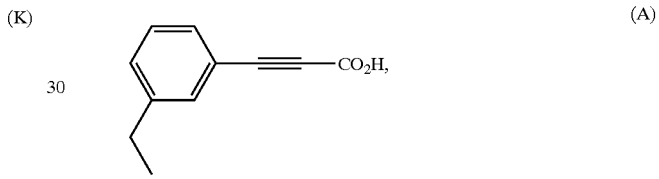
(B) 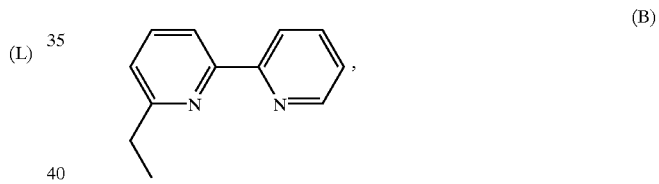
(C) 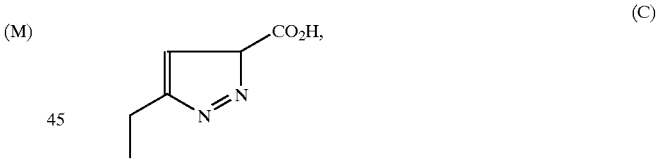
(D) 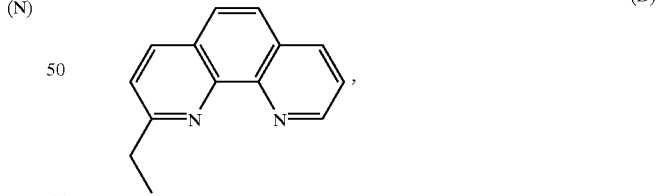
(E) 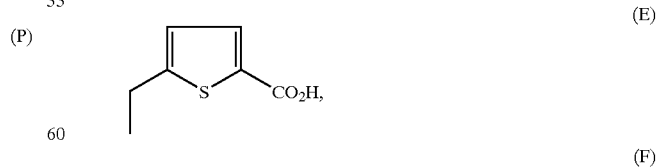
(F) 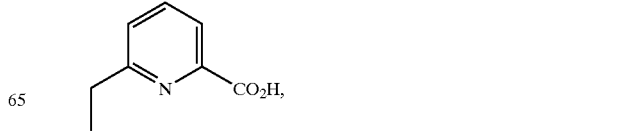

-continued

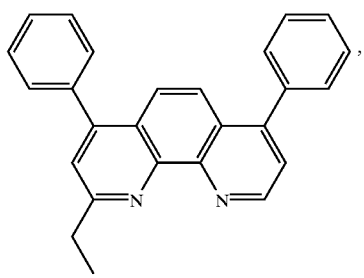

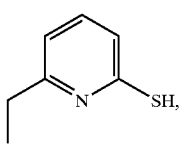

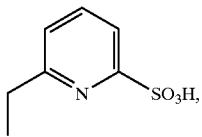

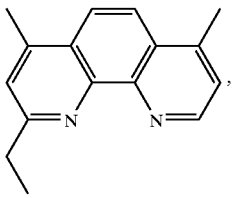

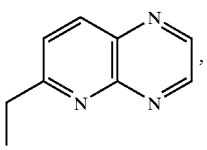

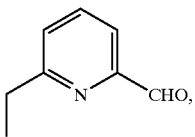

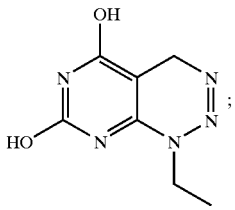

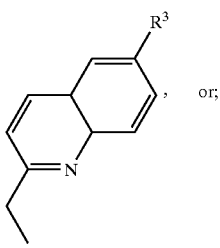

$R^2$ is methyl, ethyl, propyl, butyl or H; and
$R^3$ is F, $C_1$–$C_4$ alkyl, O($C_1$–$C_4$ alkyl) or Cl;

M is a metal ion of terbium (Tb), europium (Eu), lanthanide (La) or dysprosium (Dy); or pharmaceutically-acceptable salts thereof.

Pharmaceutical solutions of the chelates are used in preparing pharmaceutical formulations for topical application to the desired area. Advantageously, these solution are dilute compared with usual contrast agents. Thus these solutions are in the range of 0.001 M concentration irrespective of body weight, whereas with conventional pharmaceutical formulations such as MRI formulations, the concentrations of the solution are in the range of 0.5 M concentration in the vial for MRI solutions, with the dosage being based upon body weight. The formulations of the present invention are applied to the surface of the tissue such as by way of a rinse or a swab. For such surface applications, body weight is not a determining factor in the dosage.

Fluorescence images of the Golden Hamster cheek pouch tissues demonstrate the potential for using the lanthanide chelates to perform site-directed in vivo imaging.

DETAILED DESCRIPTION OF THE INVENTION

The accuracy of early stage spectroscopic imaging in soft tissue can be enhanced significantly through the use of site directed molecules (contrast agents) which concentrate in a specific tissue.

The choice of metal used in the chelates of the present invention will depend upon the color desired for the fluorescent imaging and the ligand properties. The use of terbium (Tb) or europium (Eu) are preferred as the central metal ion to render a tissue specific fluorescent probe. Derivatives of this type would be valuable for visual assessment of tissue conditions such as early detection of oral and esophagus cancer and would not depend upon protein conjugation to reach their target. Furthermore, concentration of the active fluorescent material could conceivably be much higher than in the case of immunoassays making detection much easier.

The present complexes have an excitation band of 300 to 340 nm, high quantum efficiency and millisecond relaxation lifetimes which allow signal collection after prompt tissue autofluorescence has subsided and allows data collection outside the range for normal tissue fluorescence. The present chelates permit use of a simplified and low cost imaging system, possess improved absorptivity, have larger quantum efficiencies, with longer UV wavelengths (i.e., red-shifted excitation). In contrast to other fluorescent chelates that are readily quenched in aqueous media or are at a shorted wavelength that can cause soft tissue damage, the visual fluorescence does not degenerate in water, making them well suited for animal in vivo imaging applications and the red light wave length makes them less likely to cause soft tissue damage. Furthermore, chelates derived from this family of macrocyclic ligands are among the most thermodynamically and kinetically inert lanthanide complexes, a paramount consideration for biological studies where metal ion toxicity is of major importance.

The terms used in Formulas (I) and (II) and for this invention are further defined as follows. "$C_1$–$C_4$ alkyl", include both straight and branched chain alkyl groups. An "animal" includes a warm-blooded mammal, preferably a human being. As used herein, "complex" refers to a complex of the compound of the invention, e.g. Formula (I), complexed with a metal ion, where at least one metal atom is chelated or sequestered.

As used herein, "pharmaceutically-acceptable salts" means any salt or mixtures of salts of a compound of Formula (I) or (II) that is sufficiently non-toxic to be useful in diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic, glutamic, gluconic acid, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the compounds of Formula (I) or (II) where the salt is potassium, sodium, or ammonium. Also included are mixtures of the above salts.

Of course, the free acid of the compounds of Formula (I) or (II) may be used, also the protonated form of the compounds, for example when the nitrogen atoms are protonated, i.e. when the HCl salt is formed.

Methods of Making

The complexes are prepared by methods well known in the art. Thus, for example, see Chelating Agents and Metal Chelates, Dwyer & Mellor, Academic Press (1964), Chapter 7. See also methods for making amino acids in *Synthetic Production and Utilization of Amino Acids*, (edited by Kameko, et al.) John Wiley & Sons (1974). An example of the preparation of a complex involves reacting a bicyclo-polyazamacrocyclophosphonic acid with the metal ion under aqueous conditions at a pH from 5 to 7. The complex formed results in a stable nuclide composition, e.g. stable to the disassociation of the nuclide from the ligand.

The following Scheme 1 provides a detailed discussion of the preparation of the complexes of this invention.

Scheme 1

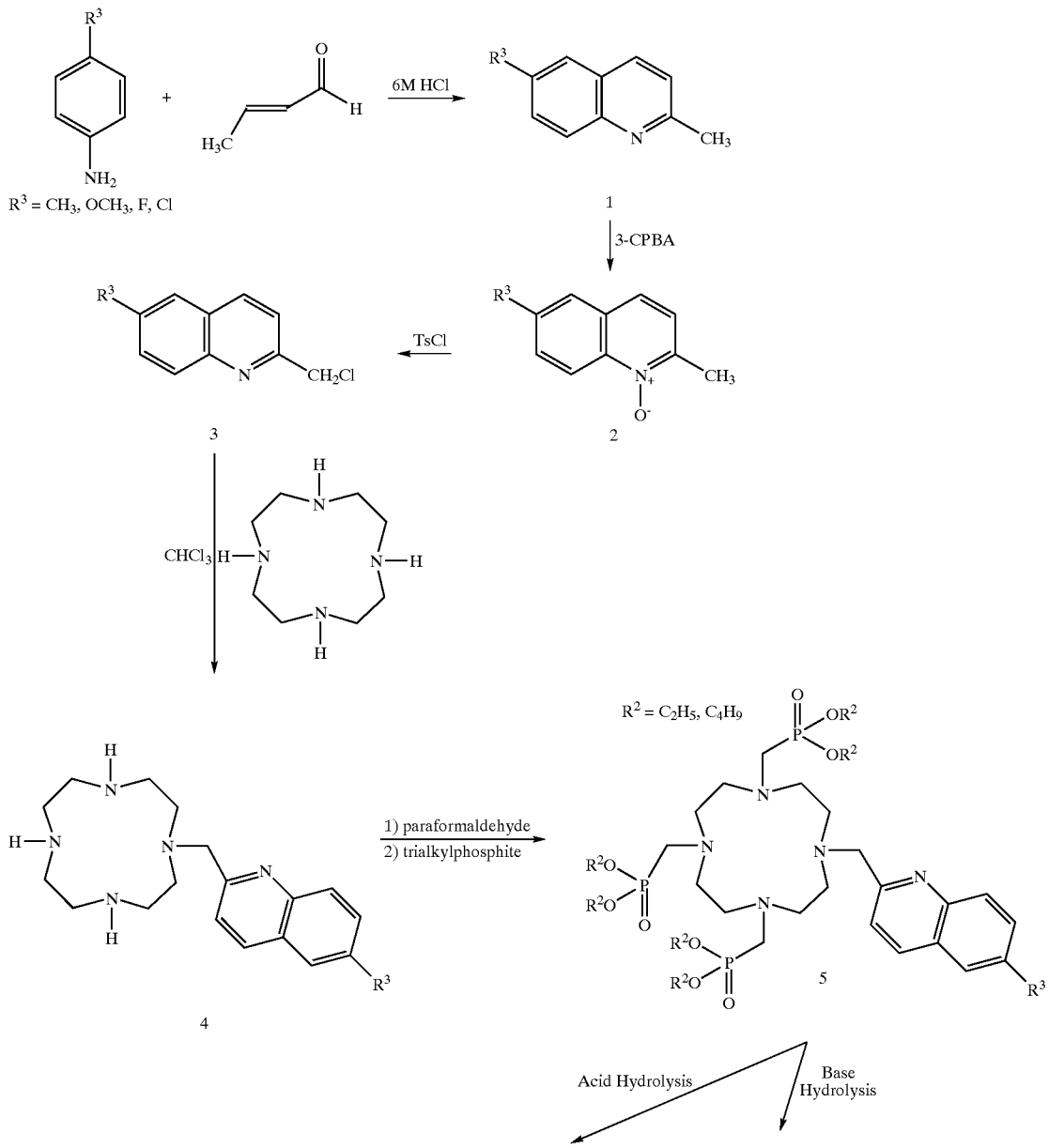

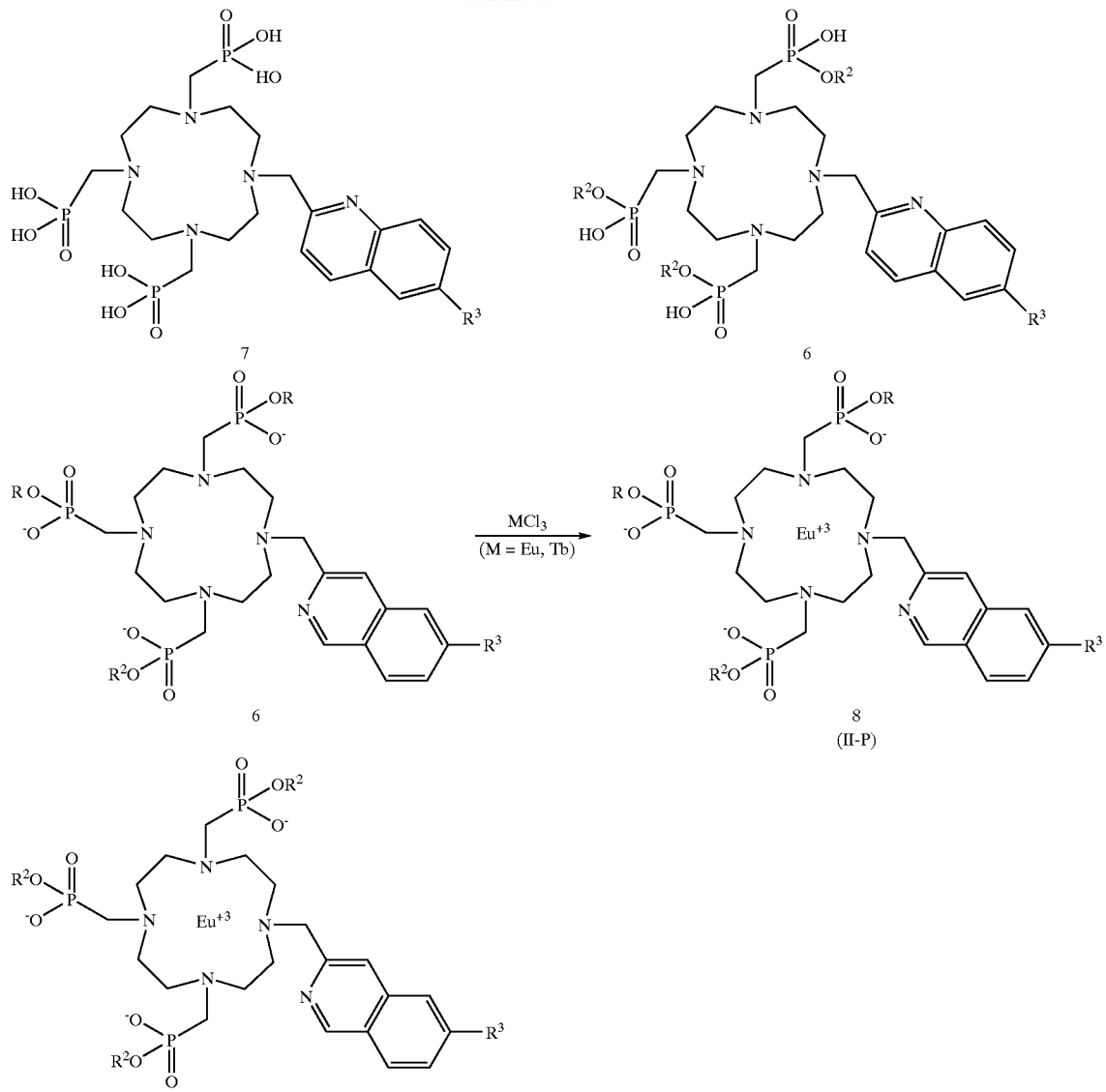

Scheme 1 shows one embodiment of the synthesis for preparing the 12-membered tetraazamacrocyclic structure possessing one quinoline moiety. Further embodiments are detailed in the examples below. 4-Substituted-aniline is reacted with butyrlaldehyde in 6M hydrochloric acid to form 2-methyl-6-substituted-quinoline (1), according to the general procedure described in J. Org. Chem. 42, 911 (1977). This quinoline compound is then reacted with 3-CPBA (3-chloro-peroxybenzoic acid) to yield, at about 98% by weight, 2-methyl-6-substituted-quinolone N-oxide (2). Deprotection with tosyl chloride (or similar deprotection agent?) and simultaneous methyl-chlorination produces 2-chloromethyl-6-substituted-quinoline (3) (35–75%, which serves as a starting material). The last two steps are by the method of John Butera and Jehan Begli [J. Med. Chem. 34, 3212 (1991].

This starting quinoline (3) is then reacted with Cyclen (1,4,7,10-teraazacyclododecane) in chloroform at room temperature to form 1-[2-(7-substituted)-methylenequinolinyl]-1,4,7,10-tetraazacyclododecane (4).

The N-alkyl phosphonate esters are then synthesized by reacting the secondary amines of the macrocycle with a trialkyl phosphite (such as tributylphosphite or triethyl phosphite) and paraformaldehyde in tetrahydrofuran (THF). The resulting phosphonate ester 5 can then be hydrolyzed under basic conditions to yield the 1-[2-(6-substituted) methylenequinolinyl]-4,7,10-tris(methylenephosphonic acid n-alkyl ester)-1,4,7,10-tetraazacyclododecane 6, or under acidic conditions to give the phosphonic acid derivative 7. These ligand systems then give the desired fluorescent chelate when complexed with the appropriate lanthanide ion such as $Tb^{+3}$, $Eu^{+3}$, or other metal ion such as La, Y, Sc, Sm, Gd, Dy, Ho, Er, Tm, Yb, and Lu.

The complexes of the present invention are administered at a ligand to metal molar ratio of at least about 1:1, preferably from 1:1 to 3:1, more preferably from 1:1 to 1.5:1. A large excess of ligand is undesirable since uncomplexed ligand may be toxic to the animal or may result in cardiac arrest or hypocalcemic convulsions.

Starting Materials

"Complex" and "chelate" are used to mean a metal ion with a ligand of Formula (I), as shown in Formula (II).

$LaCl_3$, $TbCl_3$ and $EuCl_3$ as the hexahydrate were purchased from Aldrich Chemical.

Utility

The complexes of the present invention are preferably administered as oral solutions and are useful as diagnostic agents in the manner described. These formulations may be in kit form such that the two components (i.e., ligand and metal) are mixed at the appropriate time prior to use. Whether premixed or as a kit, the formulations usually require a pharmaceutically acceptable carrier.

Indictable compositions of the present invention may be either in suspension or solution form. In the preparation of suitable formulations it will be recognized that, in general, the water solubility of the salt is greater than the acid form. In solution form the complex (or when desired the separate components) is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50 percent of the organic solvent by volume.

Indictable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethylene oxide adducts, napthalenesulfonates, alkylbenzenesulfonates, and the polyoxyethylene sorbitan esters.

For applications where a tissue is rinsed with the fluorescent chelate prior to examination, the chelate solution can vary in concentration depending upon the specific requirements. Typical concentrations for topical application are $10^{-2}$ to $10^{-7}$ M in an appropriate aqueous formulation. These concentrations are drastically lower than typical MRI contrast agents (0.5M) which are administered by IV injection at 0.1 mM/Kg body weight.

The complexes and/or conjugates can be formulated for in vivo or in vitro uses. A preferred use of the formulated conjugates is the diagnosis of diseased states (e.g., oral or esophagus cancer, colorectal, cervical) in animals, especially humans.

This invention is used with a physiologically acceptable carrier, excipient or vehicle therefore. The methods for preparing such formulations are well known. The formulations may be in the form of a suspension, indictable solution or other suitable formulations. Physiologically acceptable suspending media, with or without adjuvants, may be used.

An "effective amount" of the formulation is used for diagnosis. Advantageously, the formulation can be applied topically, which is non-invasive as compared to injectible formulations. The dose will vary depending on the disease and physical parameters of the animal, such as surface are of the tissue to be examined, the detectability of the image based on the equipment used, and the rate of chelate uptake in the diseased tissue. This latter point may be influenced by the chelate concentration and will be optimized based upon the disease type. In vivo diagnostics are also contemplated using formulations of this invention.

Methods of Using

Endoscopic Applications

The complexes of Formula (II), formed with the compounds of Formula (I) of this invention, are imaged using a method for detection of the emission, which combines microscopic interface with remote imaging technology to allow in vivo images. Methods suitable for such imaging are described in U.S. Pat. Nos. 5,928,627 and 5,507,287.

Non-Endoscopic Procedures

The chelates of the present invention are well suited to topical applications on exposed tissue such as for example, the oral cavity, skin, and cervical tissue. For these type of applications the chelates can be excited using a simple focused UV light source Theory of the Invention While not wishing to be bound by theory, it is believed that the advantageous results of the present invention are obtained because common to all chelates of this invention, the cation is positioned at an apical position above the 12-membered macrocycle and held in place through an ionic interaction with a phosphonic acid ligating group. It is this unique combination of functionalized nitrogen positions and ligating groups within the macrocyclic framework that enables chemical modifications leading to tissue selectivity.

The fluorescence of lanthanide salts such as La, Tb, Eu, and Dy in aqueous solution is very weak because the ions do not efficiently absorb the necessary energy. However, the fluorescence of these ions can be dramatically enhanced when the metal is complexed with an appropriate organic ligand.

In these unique complexes, the ligand of Formula (I) absorbs UV radiation and is excited from the ground state ($S_0$) to an excited state ($S_1$). As the ligand begins to return to its initial ground state, some of the energy is transferred from the triplet state of the ligand to an appropriate 4f energy level of the lanthanide ion. When receiving energy from the triplet state of the ligand, the ion comes to the resonance state and can undergo a radiative transition resulting in the characteristic line emission of the metal ion (ion fluorescence). In these chelate structures the ligand essentially acts as an antenna for absorbing energy which is transferred to the metal ion and re-emitted in the form of visible light. It is also advantageous to have a ligand which absorbs energy at a significantly different wavelength than what is emitted by the metal ion to minimize interference (Stoke's shift).

There have been numerous fluorescent chelates reported. A great majority of these chelates are operative in anhydrous media only because fluorescence is quenched by water. The chelates of the present invention are far superior for biological applications because of their ability to form stable, fluorescent chelates in an aqueous environment. The unique positioning of the pyridine functionality, as either part of the macrocyclic ring or as a pendant group, enables efficient energy transfer to the metal ion and also augments overall chelate stability.

The invention will be further clarified by a consideration of the following examples, which are intended to be purely exemplary of the present invention.

EXAMPLES

For the following examples, numbers in parenthesis appearing after a chemical name refer to a structure number depicted below the corresponding structures in Scheme 1.

General Experimental

NMR Data was obtained on a Bruker Spectrometer operating at 250 MHz. Samples were prepared in either $CDC_3$ or $D_2O$ with dioxane. All reported chemical shifts are reported relative to TMS (tetramethyl silane) or 1,4-dioxane as an external reference.

Absorption spectra for the ligands and chelates were obtained on a Varian/Cary 1, ultraviolet/visible spectrophotometer.

All chemicals were purchased from the Aldrich Chemical Company and used without further purification.

All parts and percentages are by weight unless otherwise specified.

Acronym Terminology for Chelates

Table A sets forth the acronyms which will be used in the following examples to represent chelants having the pendant groups listed. For all of the chelants listed in Table A, $R^1$ is quinoline (P in Formulas (I) and (II)).

TABLE A

| Example | R2 | R3 | Chelate | Acronym |
|---|---|---|---|---|
| 10 | $C_2H_5$ | $CH_3$ | Europium-QuinolylMethyl (CyclicTri-PhosphonateEthylester) | Eu-QM (CTPE) |
| 11 | $C_4H_9$ | $CH_3$ | Europium-QuinolylMethyl (CyclicTri-PhosphonateButylester) | Eu-QM (CTPB) |
| 12 | H | $CH_3$ | Europium-QuinolylMethyl (CyclicTri-Phosphonic acid) | Eu-QM (CTPH) |
| 13 | H | Cl | Europium-QuinolylMethyl (CyclicTri-Phosphonic acid) | Eu-QCl (CTPH) |
| 14 | H | F | Europium-QuinolylMethyl (CyclicTri-Phosphonic acid) | Eu-QF (CTPH) |

Starting Materials

Examples 1–3 describe the preparation of the 6-methyl substituted quinoline pendant group. The 6-chloro, 6-methoxy, and 6-flouro analogs are prepared in a similar manner by substituting the appropriate 6-chloro, 6-methoxy, or 6-flouro aniline in place of paratoluidine in scheme 1. Subsequent ligand and chelate synthesis for these other derivatives is identical to the following example.

Example 1

Synthesis of 2,6-Dimethylquinaldine (1, $R^3$=methyl)

Paratoluidine (10 g, 0.0933 mol) was dissolved in 100 mL of 6 M HCl and heated to 90° C. with vigorous stirring. Crotonaldehyde (6.62 g, 0.0945 mol) was added dropwise to the mixture over a period of 6 hours, after which the reaction was allowed to stir with heat an additional 2 hours. The completed reaction was allowed to cool to room temperature. $ZnCl_2$ (12.3 g, 0.0933 mol) was then added to the solution, which was stirred vigorously for 30 min. The solution was then cooled to 0° C. and stirred an additional 15 minutes. The precipitate was then vacuum filtered and washed with chilled 3 M HCl. The precipitate was then transferred to a beaker, stirred with isopropanol for 30 minutes, filtered, washed with additional isopropanol, and then finally with chilled ether. The solid was then transferred to a beaker to which 100 mL water was added and then chilled to 0° C. while stirring. 30 mL of $NH_4OH(aq)$ was added to the solution and allowed to stir 10 minutes. The resulting mixture was extracted with dichloromethane several times. The combined dichloromethane layers were dried using $MgSO_4$ and evaporated to afford 7.2 g (49% yield) of a dark yellow solid. The solid was recrystallized in hexanes to produce a yellow solid. $H^1$ NMR ($CDCl_3$): δ 2.50 (s, 3H), 2.70 (s, 3H), 7.23–7.45 (m, 3H), 7.94–7.99 (m, 2H).

Example 2

Synthesis of 2,6-Dimethylquinaldine N-oxide (2, $R^3$=methyl)

To a stirring solution of 2,6-Dimethylquinaldine (1) (5 g, 0.0318 mol) in 1,2 dichloroethane (130 ml) was added 3-CPBA (3-chloro-peroxybenzoic acid) (7.43 g of 72% activity, 0.0310 mol). The reaction was then heated to 40° C. for 24 hours. The completed reaction mixture was allowed to cool to room temperature, concentrated, and 10% $K_2CO_3$ and a minimal amount of ethyl acetate was to produce a two phase mixture. A precipitate then formed in both layers and was filtered, washed with water to remove traces of $K_2CO_3$ and dried to afford 4.67 g (85%). $H^1$ NMR ($CDCl_3$): δ 2.52 (s, 3H), 2.66 (s, 3H), 7.28–7.56 (m, 4H), 8.70–8.79 (m, 1H).

Example 3

Synthesis of 2-(Chloromethyl)-6-methylquinoline (3, $R^3$=methyl)

To a stirring solution of p-toluenesulfonyl chloride (6.19 g, 0.0325 mol) in dichloroethane (75 mL) was added 2,6 dimethylquinaldine N-oxide (2) (5 g, 0.0289 mol) under $N_2$. The reaction mixture was then heated to 100° C. for 24 hours, cooled, concentrated and extracted with 10% $K_2CO_3$ and ethyl acetate. The organic layer was dried with $MgSO_4$, concentrated and purified on a small silica flash column (2:1 dichloromethane:hexanes). The resulting yellow solid was then recrystallized in hexanes to afford 3.31 g (60%) of a white solid. $H^1$ NMR ($CDCl_3$): δ 2.50 (s, 3H) 4.80 (s, 2H), 7.40–7.50 (m, 2H), 7.58–7.61 (d, 1H), 8.02–8.99 (m, 1H), 8.11–8.14 (d, 1H).

Ligand Synthesis

Example 4

Synthesis of N-(6-Methyl-2-quinolylmethyl)-1,4,7,10-tetraazacyclododecane (4, $R^1$=quinolyl, $R^3$=methyl)

To a stirring solution of cyclen (3.52 g, 0.0204 mol) in chloroform (525 mL) was added 2-(Chloromethyl)-6-methylquinoline (3) (2 g, 0.0104 mol). The reaction was then allowed to stir until completion as determined by TLC, concentrated and purified on silica using a gradient elution system starting with 50:1 $CHCl_3$:MeOH; 150:4:1 $CHCl_3$:MeOH:$NH_4OH$; 100:4:1; 50:4:1; and finally with 20:4:1 to afford 2.54 g (75%) of a pale yellow oil. $H^1$ NMR ($CDCl_3$): δ 2.35–3.15 (m, 22H), 3.87 (s, 2H), 7.33–7.42 (m, 2H), 7.58–7.62 (d, 1H), 7.94–8.07 (m, 2H).

Example 5

Synthesis of N-(6-fluoro-2-quinolylmethyl)-1,4,7,10-tetraazacyclododecane (4, $R^1$=quinolyl, $R^3$=F)

To a stirring solution of cyclen (3.52 g, 0.0204 mol) in chloroform (525 mL) was added 2-(Chloromethyl)-6-fluoroquinoline (2 g, 0.0102 mol). The reaction was then allowed to stir until completion as determined by TLC, concentrated and purified on silica using a gradient elution system starting with 50:1 $CHCl_3$:MeOH; 150:4:1 $CHCl_3$:MeOH:$NH_4OH$; repeated at 100:4:1 $CHCl_3$:MeOH:$NH_4OH$; repeated again at 50:4:1 $CHCl_3$:MeOH:$NH_4OH$; and finally with 20:4:1 $CHCl_3$:MeOH:$NH_4OH$ to afford 2.54 g (75%) of a pale yellow oil that solidified on standing to an off-white solid. $H^1$ NMR ($CDCl_3$): δ 2.35–3.15 (m, 19H), 3.87 (s, 2H), 7.33–7.42 (m, 2H), 7.58–7.62 (d, 1H), 7.94–8.07 (m, 2H).

Example 6

Synthesis of N-(6-methyl-2-quinolylmethyl)-N',N",N'"-tris(methylene phosphonic acid)-1,4,7,10 tetraazacyclododecane (7, $R^1$=quinolyl, $R^2$=H, $R^3$=methyl)

To a stirring solution of N-(6-methyl-2-quinolylmethyl)-1,4,7,10 tetraazacyclododecane (4) (1 g, 0.00305 mol) in dry THF (50 mL) under $N_2$ was added paraformaldehyde (0.276 g, 0.00918 mol). The reaction was allowed to stir for 3 hours at room temperature. Tributylphosphite (2.30 g, 0.00918 mol) was then added to the mixture slowly and allowed to stir until the solution turned completely clear. The completed reaction mixture was concentrated and dried under high vacuum for 24 hours to afford a pale yellow oil. The resulting oil was dissolved in 6 M HCl (50 mL) and heated with stirring to a gentle reflux for 4 days. The solution was allowed to cool and excess HCl was removed by azeotropic distillation with water to afford a pale yellow solid. The product was then further purified if necessary by recrystallization with anhydrous isopropyl alcohol to afford 2.17 g (90%) of a white solid. The compound was isolated in its fully protonated form. $H^1$ NMR ($D_2O$): δ 2.45–3.80 (br m, 25H), 4.07 (s, 2H), 7.67–7.74 (m, 2H), 7.87–7.91 (d, 1H), 8.18–35 (qr 1H), 8.79–8.84 (d, 1H).

Example 7

Synthesis of N-(6-methyl-2-quinolylmethyl)-N',N", N'''-tris(methylene phosphonic acid butyl ester)-1,4, 7,10 tetraazacyclododecane (6, $R^1$=quinolyl, $R^2$= $C_1H_2$, $R^3$=methyl)

To a stirring solution of N-(6-methyl-2-quinolylmethyl)-1,4,7,10-tetraazacyclododecane (4) (1 g, 0.00305 mol) in dry THF (50 mL) under $N_2$ was added paraformaldehyde (0.276 g, 0.00918 mol). The reaction was allowed to stir for 3 hours at room temperature. Tributyl phosphite (2.30 g, 0.00918 mol) was then added to the mixture and allowed to stir until the solution turned completely clear. The completed reaction mixture was concentrated and dried under high vacuum for 24 hours to afford a pale yellow oil. The oil was then refluxed for four days with 27 equivalents of KOH dissolved in 20 mL of $H_2O$ with enough dioxane to achieve solubility. The resulting mixture volume was then reduced under vacuum to produce a thick oil. The oil was then washed with a series of increasing chloroform concentration methanol/chloroform solutions with filtration and removal of solvent. The resulting oil was then dissolved in a minimal amount of chloroform and acetonitrile was then added until the solution became cloudy. The mixture was allowed to stand to precipitate the pure product, which was then filtered, dissolved in water, and lypholized to produce 0.541 g (20%) of a slightly yellow solid. $H^1$ NMR ($D_2O$): δ 0.75–0.85 (m, 9H), 1.18–1.45 (m, 6H), 1.48–1.55 (m, 6H), 1.91–3.10 (br m, 19H), 3.65–3.82 (br, 12H), 4.10–4.21 (br, 2H), 7.32–7.41 (m, 1H), 7.50–7.61 (br, 1H), 7.80–7.88 (d, 1H), 7.92–8.01 (m, 1H), 8.20–8.31 (d, 1H).

Example 8

Synthesis of N-(6-methyl-2quinolylmethyl)-N',N", N'''-tris(methylene phosphonic acid ethyl ester)-1,4, 7,10 tetraazacyclododecane (6, $R^1$=quinolyl, $R^2$= $C_2H_5$, $R^3$=methyl)

To a stirring solution of N-(6-methyl-2-quinolylmethyl)-1,4,7,10-tetraazacyclododecane (4) (1 g, 0.00305 mol) in dry THF (50 mL) under $N_2$ was added paraformaldehyde (0.276 g, 0.00918 mol). The reaction was allowed to stir for 3 hours at room temperature. Triethyl phosphite (1.524 g, 0.00918 mol) was then added to the mixture and allowed to stir until the solution turned completely clear. The completed reaction mixture was concentrated and dried under high vacuum for 24 hours to afford a pale yellow oil. The oil was then refluxed for four days with 27 equivalents of KOH dissolved in 20 mL of $H_2O$ with enough dioxane to achieve solubility. The resulting mixture volume was then reduced under vacuum to produce a thick oil. The oil was then washed with a series of increasing chloroform concentration methanol/chloroform solutions with filtration and removal of solvent. The resulting oil was then dissolved in a minimal amount of chloroform and acetonitrile was then added until the solution became cloudy. The mixture was allowed to stand to precipitate the pure product which was then filtered, dissolved in water, and lypholized to produce 0.520 g (21%) of a slightly yellow, solid. $H^1$ NMR ($D_2O$): δ 0.87 (t, 6H), 1.07 (t, 3H), 2.45 (s, 3H), 2.49–3.09 (br m, 25H), 3.47 (p, 4H), 3.76 (p, 2H), 3.89 (s, 2H), 7.55 (m, 3H), 7.76 (d, 1H), 8.15 (d, 1H).

Example 9

Synthesis of N-(6-fluoro-2-quinolylmethyl)-N',N", N'''-tris(methylene phosphonic acid)-1,4,7,10 tetraazacyclododecane (7, $R^1$=quinolyl (II-P), $R^3$= F)

To a stirring solution of N-(6-fluoro-2-quinolylmethyl)-1,4,7,10 tetraazacyclododecane (1 g, 0.00302 mol) in dry THF (50 mL) under $N_2$ was added paraformaldehyde (0.298 g, 0.00942 mol). The reaction was allowed to stir for 3 hours at room temperature. Tributylphosphite (2.48 g, 0.00942 mol) was then added to the mixture slowly and allowed to stir until the solution turned completely clear. The completed reaction mixture was concentrated and dried under high vacuum for 24 hours to afford a pale yellow oil. The resulting oil was dissolved in 6 M HCl (50 mL) and heated with stirring to a gentle reflux for 4 days. The solution was allowed to cool and excess HCL was removed by azeotropic distillation with water to afford a pale yellow solid. The product was then further purified if necessary by recrystallization with anhydrous isopropyl alcohol to afford 2.17 g (90%) of a white solid. The compound was isolated in its fully protonated form. $H^1$ NMR ($D_2O$): δ 2.45–3.80 (br m, 22H), 4.07 (s, 2H), 7.67–7.74 (m, 2H), 7.87–7.91 (d, 1H), 8.18–35 (qr 1H), 8.79–8.84 (d, 1H).

Chelate Synthesis

Examples 10 and 11

Preparation of Eu-QM(CTPE) and Eu-QM(CTPB)

The potassium salt of N-(6-methyl-2-quinolylmethyl)-N', N",N'''-tris(methylene phosphonic acid butyl ($R^2$=n-butyl) or ethyl ($R^2$=ethyl) ester)-1,4,7,10 tetraazacyclododecane (6) (300 mg) was dissolved in 100 mL of distilled water. The pH of the solution, which was around 10.5 to start, was then adjusted to 6.5 using dilute hydrochloric acid. Europium chloride hexahydrate (1 equivalent) was dissolved in 50 mL of distilled water and added to the ligand solution dropwise with stirring. As the pH began to drop, it was maintained around six with a dilute potassium hydroxide solution. Addition of potassium hydroxide was terminated after all the europium salt had been added and when the pH had settled around 6.4. The solution was then lypholized, redissolved in chloroform and filtered through celite. The resulting filtrate was then concentrated producing a glassy solid. The solid was then taken up in water and filtered through a microfilter to remove $Eu(OH)_3$ and lipholized to produce a floculant white solid.

Example 12

Preparation of Eu-QM(CTPH)

The hydrochloride salt of N-(6-methyl-2-quinolylmethyl)-N',N",N'''-tris(methylene phosphonic acid )-1,4,7,10 tetraazacyclododecane (7) (300 mg) was dissolved in 100 mL of distilled water. The pH of the solution, which was around 4.5 to start, was then adjusted to 6.5 using dilute potassium hydroxide. Europium chloride hexahydrate (1 equivalent) was dissolved in 50 mL of distilled water and added to the ligand solution dropwise with stirring. As the pH began to drop, it was maintained around six with dilute potassium hydroxide. Addition of potassium hydroxide was terminated after all the europium salt had been added and when the pH had settled around 6.4. The solution was then lyophilized. The resulting solid was then taken up in water and filtered to remove $Eu(OH)_3$ and lyophilized again to produce a floculant white solid.

Example 13

Preparation of Eu-QCl(CTPH)

1-[2-(methylene)-6-chloroquinolinyl-4,7,10-tri(methylenephosphonic acid)-1,4,7,10-tetraazacyclododecane (6) (54 mg, 0.1 mmol) was initially dissolved in deionized water (1 mL) to give an aqueous solution of pH=1.3. Europium chloride hexahydrate (37 mg, 0.1 mmol) was then dissolved in water (1 mL) and added in one portion to the ligand solution with continuous stirring (pH=1.4). Sodium hydroxide (0.1 N) was then added in 50 µL portions until a pH=5.5 was sustained. Complexation was monitored by reverse phase HPLC eluting with methanol/water (80:20). The solution was then filtered through a 0.2 µm filter and freeze-dried to give the complex as a floculant white solid, which exhibited a brilliant green emission when excited with a UV lamp. The complexation was assessed by HPLC and the yield was quantitative.

Absorption spectra were generated as depicted in FIG. 1.

Example 14

Preparation of Eu-QF(CTPH)

Figure 2:
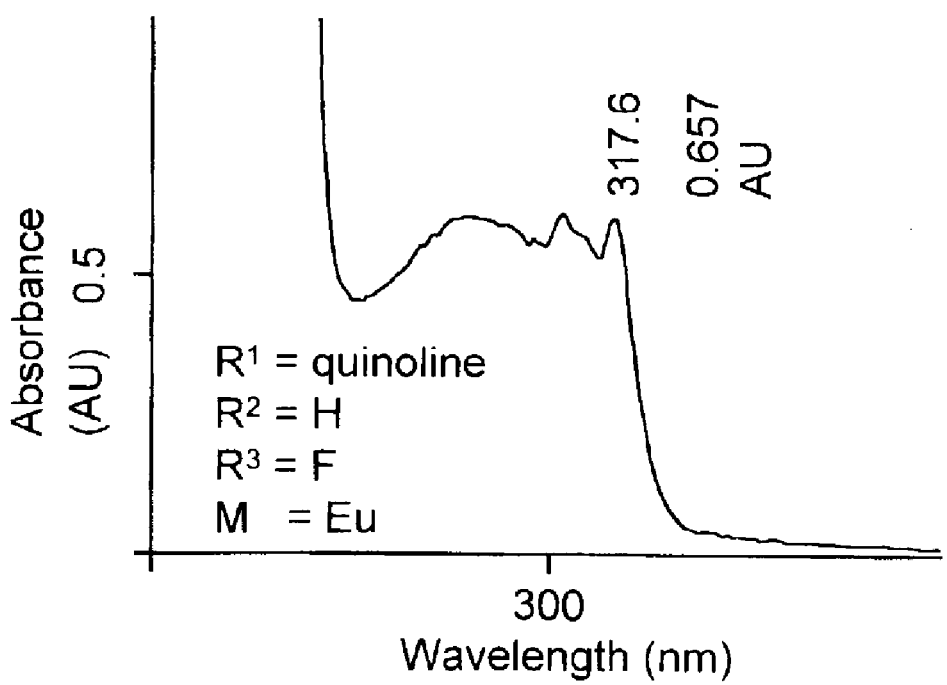
FIG. 2 is the absorption spectra for the europium chelate of Formula (II) where $R^1$ is quinolyl, $R^2$ is H, and $R^3$ is fluoro.

The potassium salt of N-(6-fluoro-2-quinolylmethyl)-N', N'',N'''-tris(methylene phosphonic acid butyl ester)-1,4,7,10 tetraazacyclododecane (300 mg, $3.34 \times 10^{-4}$ mol) was dissolved in 100 mL of distilled water. The pH of the solution, which was around 10.5 to start, was then adjusted to 6.5 using dilute hydrochloric acid. Europium chloride hexahydrate (123 mg, $3.34 \times 10^{-4}$ mol) was dissolved in 50 mL of distilled water and added to the butyl half ester solution dropwise with stirring. As the pH began to drop, it was maintained around six with a dilute potassium hydroxide solution. Addition of potassium hydroxide was terminated after all the europium salt had been added and when the pH had settled around 6.4. The solution was then lypholized, redissolved in chloroform and filtered through celite. The resulting filtrate was then concentrated producing a glassy solid. The solid was then taken up in water and filtered through a microfilter to remove $Eu(OH)_3$ and lyophilized to produce a floculant white solid. Absorption spectra were generated as depicted in FIG. 2.

Imaging

Example 15

Imaging in the Hamster Cheek Model

Malignant lesions in the Syrian hamster cheek were induced by applying topically a 0.5% solution of dimethylbenzanthracene (DMBA) in mineral oil inside the right cheek pouch three times weekly until macroscopic tumors were seen. Induction of visible tumors consistently takes 6–10 weeks. Traumatized cheek pouches with non-malignant lesions were prepared by applying topically sodium lauryl sulphate (SLS) daily for four days. Inflamed tissue develops within four days. In a blind study, a pathologist assessed the histology of all lesions.

The chelate from Example 10 (Eu-QM(CTPE)) was dissolved in a 5% ethanol solution with a concentration of 0.5 mM. Between 1.0 and 1.5 mL of the chelate solution was introduced by topical application and allowed to pool on the cheek pouch for a period of 10 minutes. After the 10 minute incubation period the tissue was washed with a 5% ethanol solution followed by washing with water and then finally wiped clean with a cue-tip to insure that the fluorescence detected was from within the tissue and not on the surface.

Figure 3:
FIG. 3 is a photograph of a hamster cheek pouch with the europium chelate of Formula (II), where R1 is quinolyl, R2 is ethyl, and R3 is methyl.

Excitation of the chelate was achieved by illuminating with 310 nm while emission was recorded by placing a 600 nm (FWHM=80 mn) filter in front of the CCD. Color photographs were obtained by using 800 speed film and a 35 mm camera with an exposure time of approximately 0.5 sec without the aid of an emission filter. FIG. 3 illustrates the results of the topical application of the chelant to the Hamster cheek pouch.

These results show that these chelants can be used to detect abnormalities as seen in animals.

It is intended that the specification and examples be considered as exemplary only, with the true scope and spirit of the invention being indicated by the following claims.

What is claimed is:

1. Tetraazamacrocyclic compounds of the formula

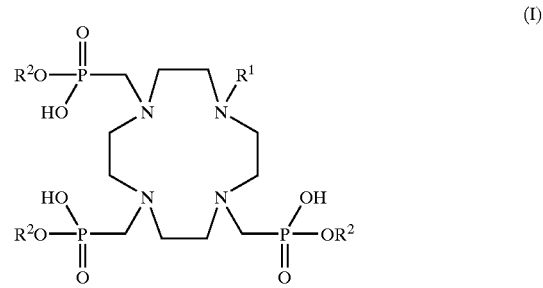

(I)

where: $R^1$ is

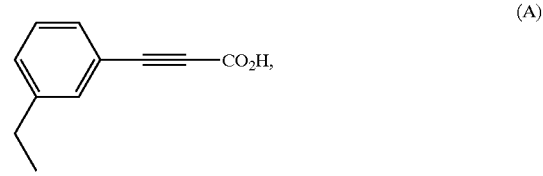

(A)

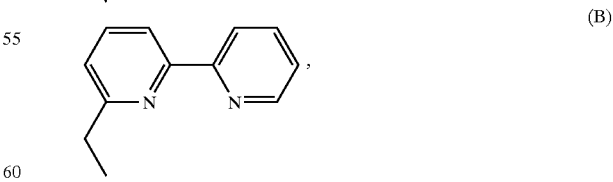

(B)

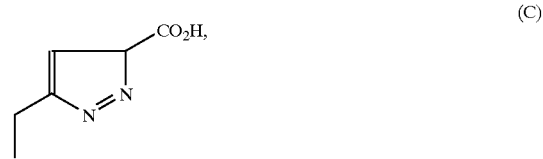

(C)

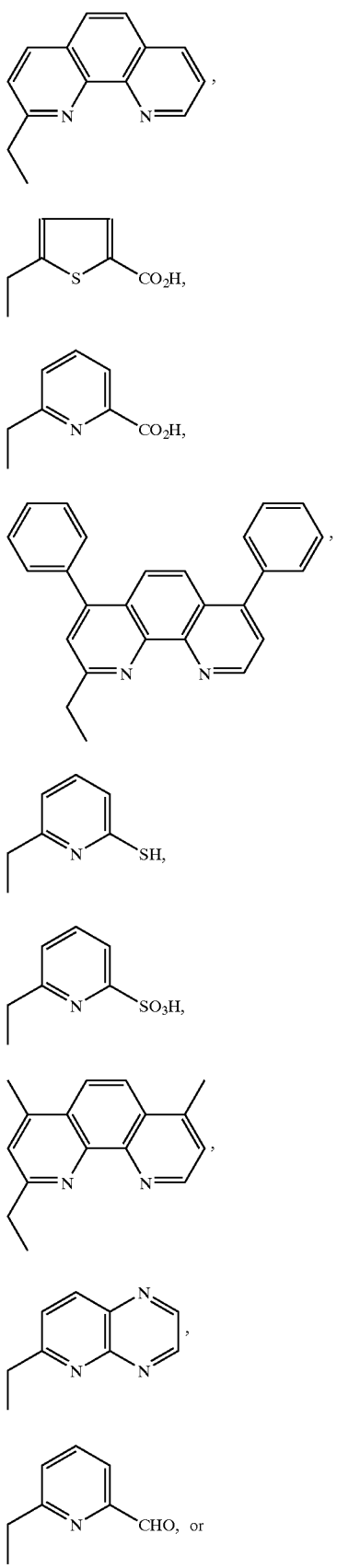
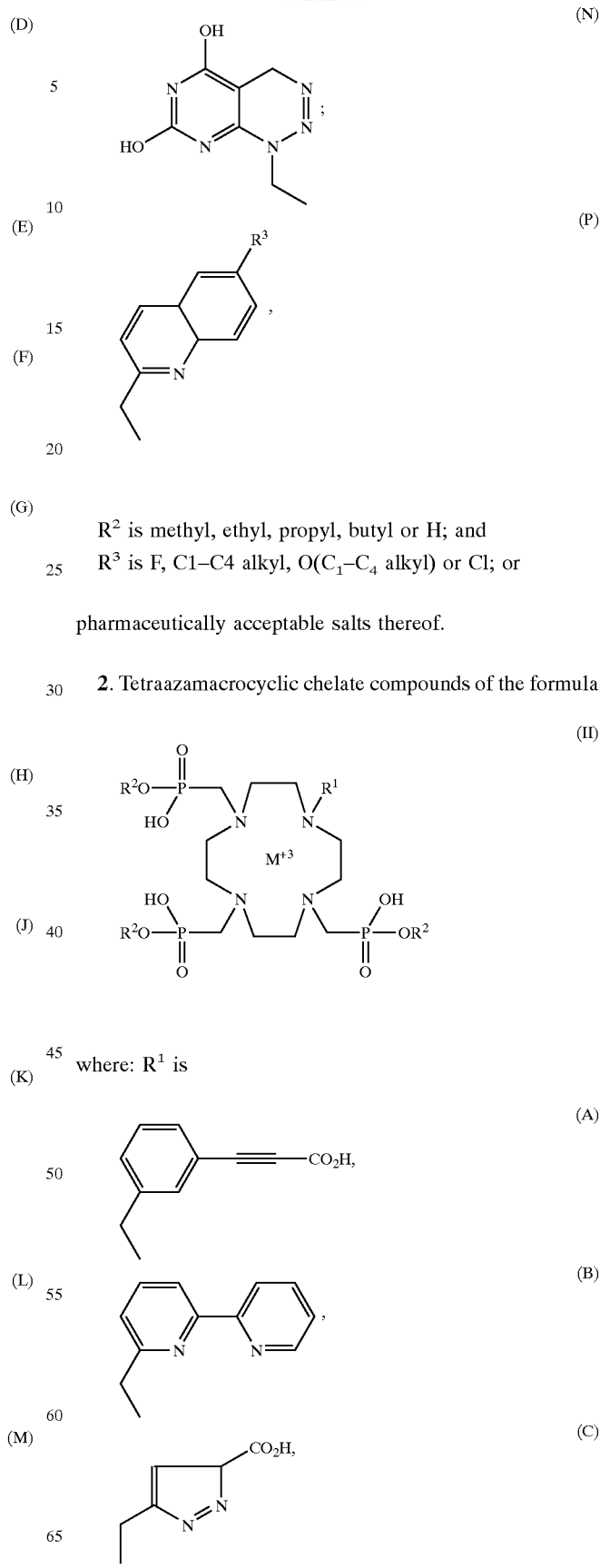
$R^2$ is methyl, ethyl, propyl, butyl or H; and
$R^3$ is F, C1–C4 alkyl, O(C$_1$–C$_4$ alkyl) or Cl; or
pharmaceutically acceptable salts thereof.
2. Tetraazamacrocyclic chelate compounds of the formula
where: $R^1$ is

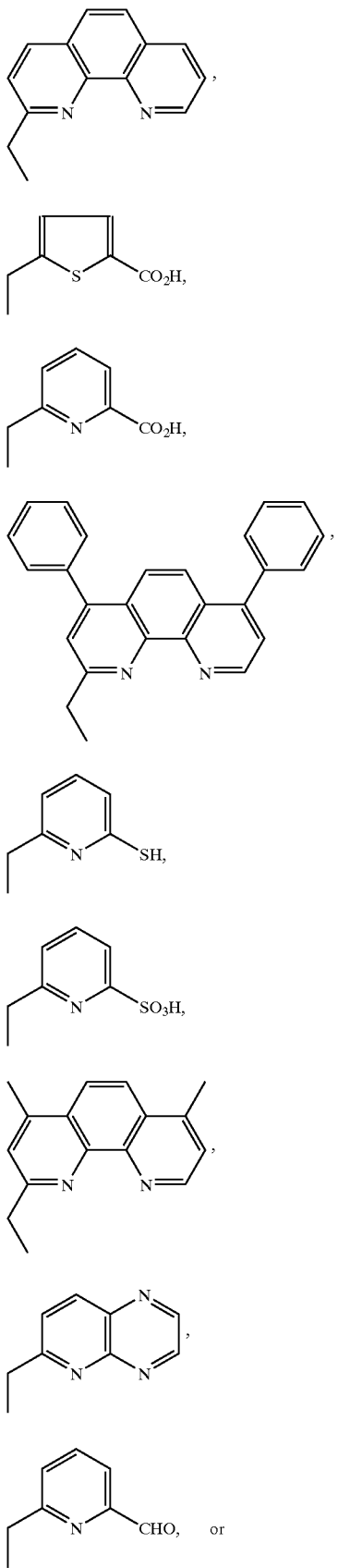

R² is methyl, ethyl, propyl, butyl or H; and
R³ is F, C1–C4 alkyl, O(C₁–C₄ alkyl) or Cl;
M is a metal ion of terbium (Tb), europium (Eu), lanthanide (La) or dysprosium (Dy); or
pharmaceutically-acceptable salts thereof.

3. Terbium 1-[2-(6-methoxy)methylenequinolinyl]-4,7,10-tri(methylene phosphonic acid)-1,4,7,10-tetraazacyclododecane.

4. Europium 1-[2-(6-methoxy)methylenequinolinyl]-4,7,10-tri(methylene phosphonic acid)-1,4,7,10-tetraazacyclododecane.

5. Europium 1-[2-(6-chloro)methylenequinolinyl]-4,7,10-tri(methylene phosphonic acid)-1,4,7,10-tetraazacyclododecane.

6. Terbium 1-[2-(6-chloro)methylene-quinolinyl]-4,7,10-tri(methylene phosphonic acid)-1,4,7,10-tetraazacyclododecane.

7. Europium 1-[2-(6-fluoro)methylene-quinolinyl]-4,7,10-tri(methylene phosphonic acid)-1,4,7,10-tetraazacyclododecane.

8. Terbium 1-[2-(6-fluoro)methylene-quinolinyl]-4,7,10-tri(methylene phosphonic acid)-1,4,7,10-tetraazacyclododecane.

9. A pharmaceutical formulation which comprises a compound of claim 1 with a pharmaceutically-acceptable carrier.

10. The formulation of claim 9 where the amount of chelate in a solution for administration is from about 0.1 mM to 5 mM.

11. A method for the diagnosis of a disease state in soft tissue in an animal which comprises administering to said animal an effective amount of the formulation of claim 9, and obtaining an image, wherein the disease state is oral, esophageal, colorectal, or cervical cancer.

12. The method of claim 11 where the formulated chelate is administered as an injectable solution or as a wash solution.

13. The method of claim 11 wherein the dose of the chelate administered topically is in solution form from about 0.1 mM to about 5 mM.

14. A method for the imaging an animal which comprises administering to said animal an effective amount of the formulation of claim 9, and obtaining an image.

15. The method of claim 12 where the image is obtained using an endoscopic fluorescence imaging microscope.

16. The method of claim 14 or 15 where the image is obtained using an UV light source.

17. The method of claim 11 wherein the disease state is oral cancer or esophagus cancer.

18. A process for preparing a complex of Formula (II) as claimed in claim 2 which comprises reacting the compound with the metal ion halide in aqueous solution.

19. The method of claim 11 wherein the UV wavelength used for detection of the chelate of claim 2 for the disease state is from 300–340 nm.

* * * * *